United States Patent
Maggi et al.

(10) Patent No.: US 6,221,395 B1
(45) Date of Patent: Apr. 24, 2001

(54) CONTROLLED RELEASE PHARMACEUTICAL TABLETS CONTAINING AN ACTIVE PRINCIPLE OF LOW WATER SOLUBILITY

(75) Inventors: Lauretta Maggi, Pavia; Ubaldo Conte, Busto Arsizio, both of (IT); Pascal Grenier; Guy Vergnault, both of St. Louis (FR); Robert Zimmer, Mulhouse (FR)

(73) Assignee: Jagotec AG, Hergiswil (CH)

( * ) Notice: Subject to any disclaimer, the term of this patent is extended or adjusted under 35 U.S.C. 154(b) by 0 days.

(21) Appl. No.: 09/144,711

(22) Filed: Sep. 1, 1998

(30) Foreign Application Priority Data

Sep. 3, 1997 (IT) .............................. MI97A2003

(51) Int. Cl.[7] .............................. A61K 9/20; A61K 9/30
(52) U.S. Cl. .................... 424/475; 424/474; 424/464; 424/468
(58) Field of Search ................... 424/464, 468, 424/472, 474, 479, 480, 475

(56) References Cited

U.S. PATENT DOCUMENTS

| | | |
|---|---|---|
| 4,839,177 | 6/1989 | Colombo et al. . |
| 5,422,123 | 6/1995 | Conte et al. . |
| 5,464,633 | * 11/1995 | Conte et al. . |
| 5,476,654 | 12/1995 | Conte et al. . |
| 5,626,874 | * 5/1997 | Conte et al. . |
| 5,780,057 | * 7/1998 | Conte et al. . |

FOREIGN PATENT DOCUMENTS 0468392   1/1992   (EP) .

OTHER PUBLICATIONS

Abstract, corresponding to Italian Patent No. 1 188 165, granted Jan. 7, 1988, in the name of Paolo La Manna.
Abstract of U.S. 5, 419,917, granted May 30, 1995, in the name of Chih–Ming Chen et al.

* cited by examiner

Primary Examiner—Thurman K. Page
Assistant Examiner—Brian K. Seidleck
(74) Attorney, Agent, or Firm—Leydig, Voit & Mayer, Ltd.

(57) ABSTRACT

It is described a new method for the preparation of pharmaceutical tablets carrying poorly soluble in water principle; this method allows to obtain tablets with fast and/or slow release of the active principle. The peculiar feature is the fact that the poorly soluble in water active principle (es: nifedipine) is treated with a surfactant, during the granulation phase or whatever during the preparation process; the obtained product, subjected to a compression, produces pharmaceutical tablets which show high bioavailability of the carried active principle. This procedure can be used to prepare polymeric matrixes (with modified release), formed by tablets with one or more layers. The procedure of manufacture and the characteristics of the new finished tablet are described.

4 Claims, 1 Drawing Sheet

CONTROLLED RELEASE PHARMACEUTICAL TABLETS CONTAINING AN ACTIVE PRINCIPLE OF LOW WATER SOLUBILITY

FIELD OF THE INVENTION AND STATE OF THE ART

Biological active agents poorly soluble in water or in biological fluids have always represented remarkable problems of bioavailability when they are administered in pharmaceutical formulations for oral use.

This problem happens both in the case of preparation of fast release tablets and, mostly, in the case of tablets and/or whatever of therapeutic systems from which the active principle has to be released in an extended interval of time.

In fact, in the case of so-called "retard" tablets, the very low solubility of the drug produces a very changeable release speed of the active principle from the pharmaceutical formulation and, as consequence, a changeable and wrong absorption and, therefore, therapeutical effect.

Practically the dissolution speed of the active principle results as the restrictive factor of the absorption process and the followed therapeutic activity.

Many attempts have been carried out to modify the parameters which influence the dissolution speed of a biological active and poorly soluble agent.

The employment of micronized active agents, which show so wide superficial area, results widely utilized and well known by the expert of the art.

In fact, the process of dissolution of an active agent is regulated of the Noyes and Withney law which is usually expressed in the following form:

$$\frac{dc}{dt} = \frac{DS(Cs - C)}{h}$$

wherein dc/dt=dissolution speed; it is the quantity of agent that dissolves in the unit of time D=diffusion coefficient of the substance (depending from the molecular weight, from the viscosity of the medium, from the temperature, etc.)

h=thickness of the diffusion layer

S=total superficial area exposed to the medium of dissolution

Cs=concentration of the agent in the diffusion layer

C=concentration of the drug in solution in mass.

Procedures of micronization have been used to increase the dissolution speed of a lot of active principles like, for example: chloramphenicol palmitate, terfenadine, nitrofurantoine, naftazone, griseofulvine, even if, in this last case, an increase of the dissolution speed gives a great increase both of the activity but mostly of the toxicity of the product.

Also in the case of nifedipine, a drug widely used in the treatment of hypertension, it is known that a rapid effect of the drug can be obtained by using the micronized product, while by using the active principle in a greater granulometry or more precisely with a superficial area lower than 5 $m^2/g$ it is obtained a retard in the dissolution speed and therefore a slower absorption speed and, consequently, a retarded therapeutical effect. This last procedure to obtain slow release pharmaceutical formulations has been claimed in German patents 2,209,526 and DE A1 3,033,991 even if the active agent with a precise granulometry and/or with a superficial area under the limits described in the quoted patent is particularly complex and not easily standardizable to obtain.

Different methods have been carried out to increase the dissolution speed of poorly soluble active agents like, for example, the transformation of the active substances from a crystalline to an amorphous state which represents, usually, an increase of the solubility and so of the dissolution speed too, for example the 1-acetoxy-ethyl-cefuroxime (axetylcefuroxime) (v. Gouda M. W. et al: Drug Develop. & Ind: Pharm. 3, 273, 1977).

To obtain similar results clathrates or inclusion complexes with polymers like polyvinylpyrrolidone, polyoxyethylenglycol, polyvinylalcohols, celluloses and derivatives have been prepared and in particular the complexes with cyclodextrins have provoked a lot of interest, even if it has to be underlined that these modifications involve a great increase of weight of the pharmaceutical formulation because at least a ratio of 1:1 molar between the drug and the polymer is usually utilized.

A wide series of possibilities to increase the dissolution speed of poorly active principles is described in the test "Technique of solubilization of drugs" of S. H. Yalkowsky-M. Dekker New York 1985.

A different technique to increase the dissolution speed of not very soluble active agent is claimed in the Italian patent no 1.188.165 (see application no 20474 A/85) and in the Italian patent no 1.246.188 and in the U.S. Pat. No. 5,476, 654 in which it is used a procedure to load the poorly soluble drug on a support formed by hydrophylic swollen polymers or through a co-mixing and/or co-grinding process.

Nevertheless, all these methods allow to obtain an increase of the dissolution speed of an active principle but they don't guarantee a better bioavailability of the same, in particular, when this poorly soluble active principle, is carried out in a pharmaceutical formulation for oral use.

Like above mentioned, an increase of the dissolution speed of a poorly soluble drug is necessary for the preparation of fast-release tablets, but mostly for modified-release tablets, in order to allow that the absorption of the drug is not limited from the speed of its solubilization.

In the particular field of the controlled or modified release, the systems able to release the active principle at constant speed during time, namely systems that are usually defined with zero-release kinetics, are great important.

In fact, for example, in the case of hydrophilic matrixes, which form the class of the most utilized and diffused pharmaceutical formulations, the release of the drug shows at the beginning the fast release of a dose fraction ("burst effect"), phenomenon which has to be avoided because it can determine the outbreak of toxic effects linked to excessive absorption.

To avoid the "burst effect" different solutions have been proposed and adopted like to save a fraction of the matrix surface with a waterproof layer, at least for a determined interval of time, like described in the U.S. Pat. No. 4,839, 177 and U.S. Pat. No. 5,422,123.

A different solution to the problem of the "burst effect" is the suggestion to add, in the formulation of the hydrophilic matrix, ionizable, pharmaceutically acceptable, compounds.

This last solution is reported in the U.S. Pat. No. 5,419, 917 in which it is described that the employment of polar substances in an hydrophilic matrix shows a great reduction of the dissolution speed of the active principle carried in the hydrophylic matrix.

DESCRIPTION OF THE INVENTION

Now we have unexpectedly found, and it is the object of the present industrial patent, that the use of particular concentrations of surface-active agents in a hydrophilic matrix, allow to obtain an increase of the dissolution speed of a poorly soluble drug and, in this way, also an improvement of the absorption and bioavailability of the active principle carried in this matrix.

These systems of matrix release, composed by pharmaceutical tablets of one or more layers, one of which contains the active principle, can be produced by using precise productive and high industrial reproducible technologies. Moreover, we have, unexpectedly found that these systems do not determine "burst effect" and especially, they allow to eliminate the variability of the absorption caused by differences in the granulometry of the poorly soluble active principle.

In this way we have carried out and experimentally proved a new therapeutic system, with modified and controlled release, that solves the problem of the "burst effect" bound to the matrix systems. This system shows innovative advantages of safety and therapeutic efficacy, because the release of the active principle happens in a complete and reproducible way and the absorption results effective and high, like it is showed by the data relative to the plasma concentrations ($C_{max}$), obtained after the administration to the healthy volunteer, as it will be reported in the examples of the present patent.

Object of the present invention is a tablet of one or more layers one of which, at least, carries the active principle while the other one, or the others layers, have mostly the function of barrier with the purpose to modulate, for a determinable period of time, the release of the carried drug from the layer including the drug (For the geometry of the systems with more layers it refers back to what described in the above U.S. Pat. No. 5,422,123).

One of the characteristics of the tablet of the invention consists in the fact that in the preparation of the treated layer (or nucleus), beyond the active principle and a surface-active agent, also polymeric substances are utilized able to modulate (to slow down and/or to speed up) the release of the active principle.

As poorly very soluble in water substances (which show a solubility at 20° C. less then 50 mg/ml) many drugs can be used, including, in order to illustrate and not to limit: nifedipine, ricardipina, nitrendipine, nimodipine, niludipine, nilvadipine, nisoldipine, fenofibrate, naftazone, terfenadine.

These poorly soluble in water active substances are included in the treated layer (or nucleus) in a percentage from 9 to 80% of the weight, preferably from 20 to 60%.

The system is characterized by the fact that in the preparation of said nucleus or layer which containing the active principle, surfactant substances or substances with hydrophilic characteristics of acceptable pharmaceutical type, are used, selected from the group consisting of:
anionic surfactants
cationic surfactants
non-ionic surfactants
polyoxyethylenglycols (PEG) with molecular weight from 200 to 200,000
copolymers to polyoxyethylenic/polyoxypropylenic blocks (Poloxamer)
N, N', N", N"' tetra-(polyoxyethylen)(polyoxypropylen) diaminoethylene (Tetronic, Poloxamine)
dimethylpolysiloxane (Simethicone).

In order to illustrate and not to limit, the substances with surfactant properties, the following ones are reported: sodium lauryl sulphate, aluminium monostereate, sodium cetostearyl sulphate, magnesium and ammonium lauryl stearate, mono-, di-, triethanolamine laurylstearate, glycerylmonostearate, glycerylmonoleate, lauromacrogols (polyethoxylated laurylic alcohol), polysorbates of different pharmaceutical degree (they usually contain from 20 to 120 mols of $C_2H_4O$), esters of sorbitane with fatty acids, alkyldimethyl-(phenylmethyl) ammonium hydrochloride, cholesterol, bile acids and relative salts or esters or derivatives, lecithines, nonoxynoles or macrogolnonylphenylethers (polyethoxylated nonylphenols).

Said surfactants can be added to the active agent either with simple mixing or, in the case of a previously prepared granulated, using other components, too, like coadjuvants. These surfactants can be added, for example, to the binder solution, like it is well known in the prior art.

These hydrophyle or surfactants substances are included in the pharmaceutical formulation in a percentage from 1% to 40% of the weight of the treated layer, preferably from 2% to 30%.

As polymeric substances in the preparation of said layer (or nucleus) can be used, for example, reticulated polyvinylpyrrolidone, hydroxypropylmethylcellulose, reticulated sodium carboxymethyl-cellulose, carboxymethylstarch, potassium methacrylate-divinylbenzene copolymer, polyvinylalcohols, hydroxypropylcellulose at molecular weight from 2,000 to 4,000,000, carboxyvinylpolymers, glucanes, scleroglucanes, mannanes, galattomannanes, gellanes, xanthanes, alginic acid and derivatives, polyanhydrydes, polyaminoacids, poly-(methyl vinyl ethers/maleic anhydryde), carboxymethylcellulose and derivatives, ethylcellulose, methylcellulose and in general cellulosic derivatives, starchs, starch derivatives, alfa, beta, gamma cyclodextrins and in general dextrin derivatives.

These polymeric substances form from 3% to 90% of the weight of the layer (or nucleous), but preferably from 5% to 50%.

For all above polymers, many types characterized by different chemical and physical properties, solubility and gelling are present in the market, in particular, regarding the hydroxypropylmethylcellulose many types with different molecular weight (from 1,000 to 4,000,000) and different level of substitution can be used. Said types of hydroxypropylmethylcellulose show different characteristics because they are usually erodible and able to produce gels, by the way of the viscosity and the degree of substitution (D.S.) shown in the polymeric chain.

At least, usually in pharmaceutical technique excipients like: mannitol, lactose, sorbitol, xylitol, talc, stearic acid, sodium benzoate, magnesium stearate, colloidal silica and others like glyceryl monostearate, hydrogenated ricine oil, waxes, mono, bi-, trisubstituted glycerides, glycerilpalmitostearate, glyceryl behenate, cetylic alcohol can be used.

When it is desired to allow the penetration of water and/or aqueous fluids in the layer or nucleous, hydrophilic diluents are included like mannitol, lactose, starchs of different source, sorbitol, xylitol, or to carry in the formulation moistening substances and/or in general favouring the penetration of water in the compact. When it is desired to slow down the penetration of water and/or aqueous fluid in the treated layer or nucleus, hydropholic diluents are included like glyceryl monostearate, hydrogenated castor oil, waxes, mono-bi-trisubstituted glycerides. Moreover substances can be used like diluents, binders, lubricants, buffers, not adhesives, glydants, plasticizers and other substances, able to give to this layer the wanted characteristics like in the examples afterwards reported.

The pharmaceutical tablets of the invention have the advantage to release the carried active principle in a programmed way.

The system, in the simplest achievement, is a tablet with one or more layer at least one of which contains the active agent.

The formulation of the "barrier" layers includes polymeric substances and coadjuvants and plasticizer substances; when this tablet is of three layers called "barrier", they either can be similar one each other both for the composition and the thickness or they can be different.

The polymeric substances carried out in the different "barrier layers" are reported in the previous description of the nucleus or treated layer.

These polymeric substances occur in a percentage from 5% to 90% of the total weight of this layer and preferably from 50% to 90%.

Similarly, for the preparation of said layers, the coadjuvant substances previous described can be utilized.

It is possible to produce these systems with one or more layers, by using installations and equipments of widely consolidate use in pharmaceutical field and able to assure a safe and precise realization of the system with not much expensive cost (es: Elisabeth Hata).

Over these finished tablets, further polymeric coating material can be applied in order to cover the system, and to allow a protection for the tablet or a protection against light for the photosensitive active principle carried by this tablet or it can be a further slowing down in the beginning phase of the release.

Said coating can be soluble in an acid medium or permeable or it can be gastric resistant and enterosoluble, in order to allow the activation of the system only after the arrival of the tablet in the intestinal tract.

For the coating of these systems, the classical materials for the sugar coating or either natural and/or synthetic rubbers, like shellac, sandarac rubber, etc. or lypophylic material like natural waxes (white or yellow) or semi-synthetic derivatives can be used.

Moreover film forming polymeric materials can be used, like: cellulose derivatives (hydroxypropylmethylcellulose, hydroxyethylcellulose, hydroxypropylcellulose and their derivatives), acrylic and methacrylic copolymers of different molecular weight. In order to obtain the gastric resistance, many materials can be employed, like: zein, cellulose acetophthalate, cellulose acetopropionate, cellulose trimellitate, polyvinyl acetate phthalate, acrylic and methacrylic polymers and copolymers of different molecular weight and with a solubility that depends from different values of pH.

Said materials can be applied on the finished pharmaceutical formulation (tablet with one or more layers) through the classic method of film coating by using solutions in organic solvents or aqueous dispersions and working with a basin for atomization or in fluidized bed.

Said both gastric-soluble or gastric-resistant and enterosoluble materials can be employed in association with other retardant polymers and in association with other substances which have the function of plasticizers like: triethylcitrate, diethylphthalate, benzylbenzoate, dibutylsebacate, sorbitol, propylenglycol, diacetin, triacetin, dibutylphthalate, tributylacetate, castor oil, cetyl alcohol, cetylstearyl alcohol, fatty acids, polyoxyethylenglycols, usually selected from the group having a molecular weight from 200 to 200,000.

The coating layer can be applied, too, through the method of dry coating by using the above described materials, possibly previously granulated, like every expert of the field well knows.

The examples and the obtained results in the described experimental trials put better in evidence the characteristics and the functionalities of the new system. In any case, the innovation of the realization is characterized by the fact that the claimed therapeutic system can be obtained by using the usually productive technologies, that is the system is transferable in an industrial process.

EXAMPLE 1

Figure 1:
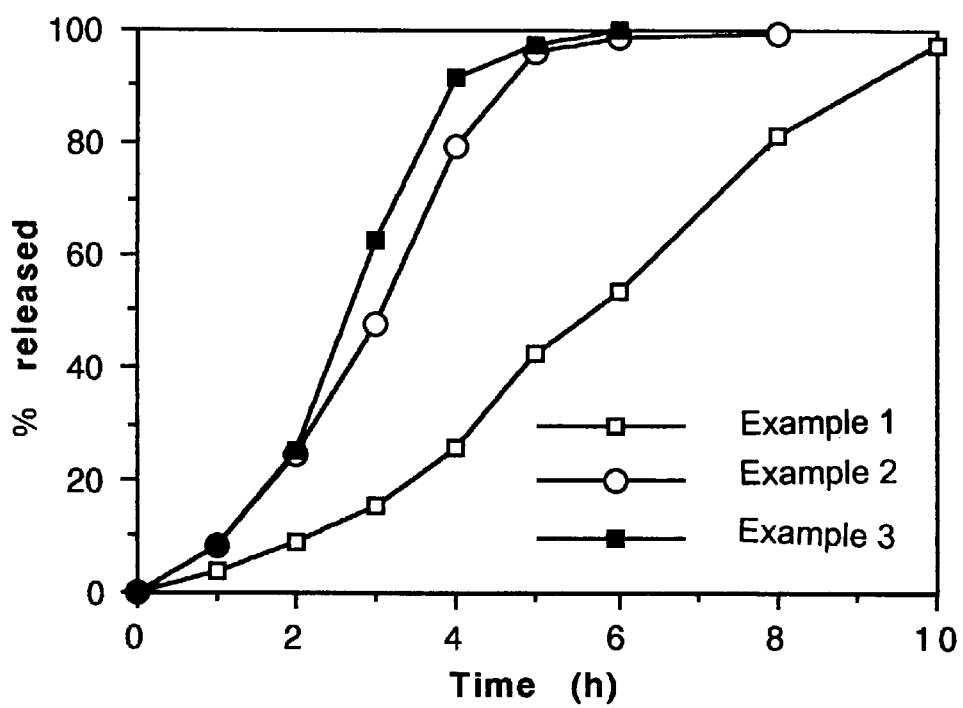
FIG. 1 shows the drug release in percent on the starting whole content, during the time, for the tablets according to Example 1, 2, and 3.

Preparation of a series of (5,000) tablets containing nifedipine 60 mg as active principle.

1-a-Composition of the first layer:

|  |  | % weight |
|---|---|---|
| Nifedipine (0.5 m²/g) | 60.0 mg | 41.66 |
| Lactose monohydrate (USP grade) | 40.0 mg | 27.77 |
| Hydroxypropylmethylcellulose (Methocel K100 M, Colorcon, Orpington, UK) | 20.0 mg | 13.88 |
| Polyvinylpyrrolidone (Plasdone K29-32, I.S.P., Wayne, NY, USA) | 10.0 mg | 6.94 |
| Sodium laurylsulphate | 10.0 mg | 6.94 |
| Magnesium stearate (C. Erba, Milano, I) | 2.0 mg | 1.4 |
| Colloidal silica (Syloid 244, Grace GmbH, Worms, D) | 2.0 mg | 1.4 |
| Total | 144.0 mg |  |

1-b-Composition of the second layer:

| Hydroxypropylmethylcellulose (Methocel E50 Premium, Colorcon, Orpington, UK) | 36.65 mg |
|---|---|
| Lactose monohydrate (USP grade, C. Erba, Milano, I) | 38.15 mg |
| Glyceryl behenate (Compritol 888ATO Gattefossé Saint Priest, F.) | 18.80 mg |
| Polyvinylpyrrolidone (Plasdone K29-32 ISP Corp., Wayne, NY, USA) | 5.00 mg |
| Yellow iron oxyde (Eingemann-Veronelli, Milano, I.) | 0.10 mg |
| Magnesium stearate (USP grade, C. Erba, Milano, I.) | 0.90 mg |
| Colloidal silica (Syloid 244, Grace GmbH, Worms, D) | 0.40 mg |
| Total | 100.0 mg |

A quantity of granulate necessary to obtain 5,000 tablets with two layers is prepared.

The procedure of manufacture consists in the preparation of a wet granulate by using sigma mod. Erweka type K 5 mixer (Frankfurt a. M., D.), and by wetting the mixture of powders with an aqueous solution of polyvinylpyrrolidone at 10% (w/v) in which (in the case of the granulate of the first layer) the sodium laurylsulphate has been solubilized. The granulate is dried in a fluid bed apparatus (Aeromatic mod. Strea) and then added up by lubricants.

1-c-Preparation of systems with two layers (by compression).

The obtained granulates, like previously reported and according schemes well known by all the experts of the field, are carried out on the two charging hoppers of a rotary compression equipment which is suitable to produce two layer tablets (es. Elisabeth Hata). In particular in the first one the described granulate at 1-b point is carried; while in the second charging hopper the previously described granulate at 1-a point is carried.

The compression equipment, equipped with punches of 7.0 mm of diameter, is regulated in order to produce systems with two layers which are formed by a first layer of 144.0 mg containing the active principle (60 mg nifedipine) and by a second layer of 100 mg of barrier granulate.

1-e-Coating process of systems with two layers.
Composition of the coating:

| | |
|---|---|
| Copolymer of the acrylic and metacrylic acid (Eudragit L30 D Rohm Pharma, D) | 10.70 mg |
| Triethylcitrate (C, Erba, Milano, I) | 1.60 mg |
| Iron oxyde | 0.20 mg |
| Total | 12.50 mg |

The film forming process is done by using a coating apparatus (a basin) for rapid coating (Manesty Accela-Cota) by spraying, through an "air less" system an aqueous dispersion at the 30% of acrylic and metacrylic acid copolymer (Eudragit L 30 D) in which the triethylacetate is solubilized.

A temperature of about 40–50° C. is used for the entrance air, according to the known art, obtaining tablets completely covered by a uniform coating film of the previously reported polymeric materials.

EXAMPLE 2

Preparation of a series of (5,000) tablets containing Nifedipine 60 mg as active principle.

A two layers tablet is prepared with a composition exactly identical to that reported in the example 1 with only the substitution in the first layer formulation of the hydroxypropylmethylcellulose (Methocel K 100 M,) 20.0 mg with an identical quantity of hydroxypropylmethylcellulose (Methocel K 15 M). The second layer maintains identical composition.

EXAMPLE 3

Preparation of a series of (5,000) tablets containing Nifedipine 60 mg as active principle.

A two layers tablet is prepared with a composition exactly identical to that reported in the example 1 with only the substitution in the first layer formulation of the hydroxypropylmethylcellulose (Methocel K 100 M,) 20.0 mg with an identical quantity of hydroxypropylmethylcellulose (Methocel K 4 M). The second layer maintains identical composition.

f-Dissolution test
Example no 1, example no 2, example no 3:

In order to estimate the characteristics of the active principle release by the prepared and described systems in the example 1, 2, and 3, the apparatus 2 is used, paddle(USP XXII) by working at 100 r.p.m. and using as dissolution fluid 1 l of buffer solution at pH 6.8 formed by tris-hydroxymethylaminomethane 0.1M, which contains 1% of polysorbate 80. The release of the active principle is followed through the spectrophotometric UV determination by using an automatic system of sampling and reading (Beckman).

The results of the trials are reported in table 1.

TABLE 1

| Time (h) | % released Example n°1 | % released Example n°2 | % released Example n°3 |
|---|---|---|---|
| 1 | 3.8 | 8.1 | 8.1 |
| 2 | 9.2 | 24.6 | 25.0 |
| 3 | 15.4 | 47.7 | 62.7 |
| 4 | 25.8 | 79.2 | 91.5 |
| 5 | 42.3 | 96.1 | 97.3 |
| 6 | 53.5 | 98.5 | 99.7 |
| 8 | 81.5 | 99.1 | 101.0 |
| 10 | 97.3 | | |

From the analysis of table 1, it's evident that the utilization of hydroxypropylmethylcellulose of different molecular weight deeply modifies the release speed of the active principle. In particular in the example 1 hydroxypropylmethylcellulose is used at high molecular weight (Methocel K 100 M,) in the example 2 hydroxypropylmethylcellulose is employed at medium molecular weight (Methocel K 15 M) and in the example 3 at low molecular weight (Methocel K 4M) (see FIG. 1, too).

"In vivo" trials

In order to estimate the characteristics of bioavailability of the active principle carried out in the pharmaceutical formulation described in the example 1, a "cross over" experiment has been done with 12 healthy volunteers by using the medical speciality Procardia XL, as reference formulation, containing the same quantity of nifedipine.

In particular the following parameters has been determined:

$C_{max}$=maximum haematic concentration (peak) in ng/ml
$T_{max}$=time to achieve the peak
AUC(o–inf)=area under curve from 0 to infinity The results are expressed as percentage in respect to the reference formulation.
$C_{max}$=91.0%
$T_{max}$=73.3%
AUC (o–inf)=90.9%

From the "in vivo" reported data, the pharmaceutical formulation described in the example 1 results bioequivalent in respect to the reference formulation, being AUC clearly over the 80%.

EXAMPLE 4

Preparation of a series of (5,000) tablets containing Nifedipine 60 mg as active principle.

A two layer tablet is prepared with a composition exactly identical to that reported in the example 1 with the only substitution in the first layer formulation of the quantity of sodium laurylsulphate used: instead of 10.0 mg 15.0 mg are employed. The method of production is the same too. The second layer maintains identical composition.

EXAMPLE 5

Preparation of a series of (5,000) tablets containing Nifedipine 60 mg as active principle.

A two layer tablet is prepared with a composition exactly identical to that reported in the example 1 with the only substitution in the first layer formulation of the quantity of sodium laurylsulphate used: instead of 10.0 mg, 20.0 mg are employed. The method of production is the same too. The second layer maintains identical composition.

EXAMPLE 6

Preparation of a series of (5,000) tablets containing Nifedipine 60 mg as active principle.

A two layer tablet is prepared with a composition exactly identical to that reported in the example 1 with the only substitution in the first layer formulation of the quantity of sodium laurylsulphate used: instead of 10.0 mg, 30.0 mg are employed. The method of production is the same too. The second layer maintains identical composition.

Dissolution test
Example no 4, Example no 5, Example no 6

In order to estimate the characteristic of the active agent release by the prepared and described systems in the example 4, 5, and 6, the apparatus 2 is used, paddle(USP XXII) by working at 100 r.p.m. and using as dissolution fluid 1 l of buffer solution at pH 6.8 composed by tris-hydroxymethylaminomethane 0.1M, which contains 1% of polysorbate 80. The release of the active agent is followed through the spettrophotometric UV determination by using a automatic system of sampling and reading (Beckman).

The results of the trials are reported in table 2.

TABLE 2

| Time (h) | % release Example n°4 | % release Example n°5 | % release Example n°6 |
|---|---|---|---|
| 1 | 6.6 | 6.8 | 16.9 |
| 2 | 12.9 | 15.4 | 50.8 |
| 3 | 23.1 | 43.1 | 83.8 |
| 4 | 41.5 | 71.9 | 96.2 |
| 5 | 61.5 | 90.7 | 99.6 |
| 6 | 79.2 | 99.5 | |
| 7 | 88.5 | | |
| 8 | 96.2 | | |
| 9 | 99.2 | | |
| 10 | 100.3 | | |

Figure 2:
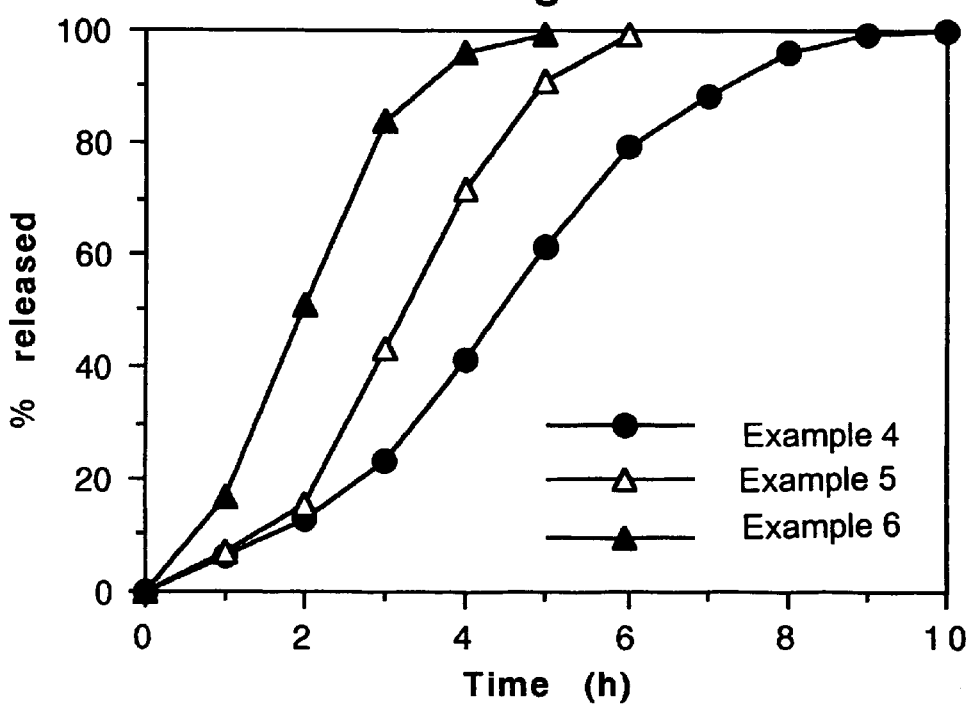
FIG. 2 shows a drug release in percent on the starting whole content, during the time, for the tablets according to Example 4, 5, and 6.

From the analysis of table 2 it appears evident that the employment of growing quantities of sodium laurylsulphate in the preparation determines a great increase of the of release speed of the active principle from the pharmaceutical formulation (see FIG. 2, too).

EXAMPLE 7

Preparation of a series of (5,000) tablets containing Nifedipine 60 mg as active principle.

7-a-Composition of the first layer:

| | | % weight |
|---|---|---|
| Nifedipine (0.5 m²/g) | 60.0 mg | 41.66 |
| Lactose monohydrate (USP grade) | 30.0 mg | 20.83 |
| Hydroxypropylmethylcellulose (Methocel K100 M, Colorcon, Orpington, UK) | 30.0 mg | 20.83 |
| Polyvinylpyrrolidone (Plasdone K29-32, I.S.P., Wayne, NY, USA) | 10.0 mg | 6.94 |
| Polyaxyethylen glycol (Gattefosse Saint Priest, F) | 10.0 mg | 6.94 |
| Magnesium stearate (C. Erba, Milano, I) | 2.0 mg | 1.4 |
| Colloidal silica (Syloid 244, Grace GmbH, Worms, D) | 2.0 mg | 1.4 |
| Total | 144.0 mg | |

7-b-Composition of the second layer:

| | | % weight |
|---|---|---|
| Hydroxypropylmethylcellulose (Methocel E50 Premium, Colorcon, Orpington, UK) | 26.77 mg | 38.34 |
| Lactose monohydrate (USP grade, C. Erba, Milano, I) | 26.77 mg | 38.34 |
| Glyceryl behenate (Compritol 888ATO Gattefosse Saint Priest, F.) | 12.89 mg | 18.41 |
| Polyvinylpyrrolidone (Plasdone K29-32 ISP Corp., Wayne, NY, USA) | 2.45 mg | 3.5 |
| Yellow iron oxide (Eingemann-Veronelli, Milano, I.) | 0.07 mg | 0.1 |
| Magnesium stearate (USP grade, C. Erba, Milano, I.) | 0.70 mg | 1 |
| Colloidal silica (Syloid 244, Grace GmbH, Worms, D) | 0.35 mg | 0.5 |
| Total | 70.0 mg | |

A quantity of granulate necessary to obtaining 5,000 tablets with two layers is prepared.

The procedure of manufacture consists in the preparation of a wet granulate by using sigma mod. Erweka type K 5 mixer (Frankfurt a. M., D.), and by wetting the mixture of powders with an aqueous solutions of polyvinylpyrrolidone at 10% (w/v) in which (in the case of the granulate of the first layer) the polyoxyethylenglycol has been solubilized. The granulate is dried in a fluid bed apparatus (Aeromatic mod. Strea) and then added up by lubricants.

7-c-Preparation of systems with two layers (by compression).

The obtained granulates, like previously reported and like schemes well known by all the experts of the field, are carried out on the two charging hoppers of a rotary compression equipment which is suitable to produce two layers tablets (es. Elisabeth Hata). In particular in the first one the described granulate at 7-b point is carried; while in the second charging hopper the previously described granulate at 7-a point is carried.

The compression-equipment, equipped with punches of 7.0 mm of diameter, is regulated in order to produce systems with two layers which are formed by a first layer of 144.0 mg including the active principle (like 60 mg nifedipine) and by a second layer of 70 mg of barrier granulate.

EXAMPLE 7

Dissolution test.

In order to estimate the characteristic of active principle release by the prepared and described system in the example 7, the apparatus 2 is used, paddle(USP XXII) by working a 100 r.p.m. and using as dissolution fluid 1 l of distilled water, which contains 1% of polysorbate 80. The active principle release is followed through the spectrophotometric UV determination by using an automatic system of sampling and reading (Beckman).

The results of the trials are reported in table 3

TABLE 3

| Time (h) | % released Example n°7 |
|---|---|
| 1 | 2.2 |
| 2 | 5.0 |
| 4 | 12.0 |
| 6 | 21.4 |
| 8 | 31.2 |
| 10 | 40.4 |
| 12 | 49.5 |
| 16 | 67.4 |
| 20 | 84.6 |
| 24 | 98.8 |

"In vivo" trials

In order to estimate the characteristics of bioavailability of the active principle carried in the pharmaceutical formulation described in the example 7, a "cross over" experiment has been done with 12 healthy volunteers by using the medical speciality Procardia XL, as reference formulation, containing the same quantity of nifedipine.

In particular the following parameters has been determined:

$C_{max}$ and AUC

The results are referred as percentage compared to the reference formulation:

$C_{max}$=123.3%

AUC (0–inf)=90.8%

From the "in vivo" reported data, the pharmaceutical formulation described in the example 7 results bioequivalent in respect to the reference formulation, being AUC clearly over the 80%.

What is claimed is:

1. A pharmaceutical tablet for oral administration, able to release under controlled speed, nifedipine, said tablet, consisting essentially of at least one first layer obtained by compression of a mixture of ingredients in the form of a powder or granulate, said first layer comprising 9% to 80% by weight of nifedipine based on the total weight of said first layer, said first layer further comprising sodium lauryl sulfate at a ratio of 6:1 by weight of the nifedipine and 3% to 90% of hydroxypropylmethylcellulose having a viscosity of 100,000 cps; one or more barrier layers which comprise from 5% to 90% of a component selected from the group consisting of pharmaceutically acceptable and biocompatible polymeric substances, based on the total weight of said barrier layer or layers having either the properties to swell or to form gels or slowly erode in contact with water or aqueous fluids and which control the release of the active principle, and a coating layer which completely covers said at least one first layer and said barrier layer, said coating layer comprising a copolymer which comprises acrylic and methacrylic acid.

2. A pharmaceutical tablet for oral administration, able to release under controlled speed, an active principle, having a water solubility at 20° C. which is lower than 50 mg/ml, said tablet consisting essentially of at least one first layer obtained by compression of a mixture of ingredients in the form of a powder or granulate, said first layer comprising 9% to 80% by weight of the active principle, based on the total weight of said first layer, said first layer further comprising sodium lauryl sulfate at a ratio of 6:1 by weight of the active principle and 3% to 90% of hydroxypropylmethylcellulose having a viscosity of 100,000 cps; one or more barrier layers which comprise from 5% to 90% of a component selected from the group consisting of pharmaceutically acceptable and biocompatible polymeric substances, based on the total weight of said barrier layer or layers having either the properties to swell or to form gels or slowly erode in contact with water or aqueous fluids and which control the release of the active principle, and a coating layer which completely covers at least one first layer and said barrier layer, said coating layer comprising a copolymer which comprises acrylic and methacrylic acid.

3. The pharmaceutical tablet of claim 2, wherein the active principle is selected from the group consisting of nifedipine, nicardipine, nitrendipine, nimodipine, niludipine, nilvadipine, nisoldipine, fenofibrate, nafiazone, and terfenadine.

4. A pharmaceutical tablet for oral administration, able to release under controlled speed, an active principle selected from the group consisting of nifedipine, nicardipine, nitrendipine, nimodipine, niludipine, nilvadipine, nisoldipine, fenofibrate, naftazone, and terfenadine, said tablet consisting essentially of at least one first layer obtained by compression of a mixture of ingredients in the form of a powder or granulate, said first layer comprising 9% to 80% by weight of the active principle based on the total weight of said first layer, said first layer further comprising sodium lauryl sulfate at a ratio of 6:1 by weight of the active principle and 3% to 90% of hydroxypropylmethylcellulose having a viscosity of 100,000 cps; one or more barrier layers which comprise from 5% to 90% of a component selected from the group consisting of pharmaceutically acceptable and biocompatible polymeric substances, based on the total weight of said barrier layer or layers having either the properties to swell or to form gels or slowly erode in contact with water or aqueous fluids and which control the release of the active principle, and a coating layer which completely covers at least one first layer and said barrier layer, said coating layer comprising a copolymer which comprises acrylic and methacrylic acid.

* * * * *